United States Patent
De Boni et al.

(10) Patent No.: US 7,559,956 B2
(45) Date of Patent: Jul. 14, 2009

(54) USE OF A CATIONIC HYDROTROPE FOR THE DIRECT DYEING OF KERATINOUS FIBRES, COMPOSITION COMPRISING IT AND COLOURING PROCESSES EMPLOYING IT

(75) Inventors: Maxime De Boni, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/798,939

(22) Filed: May 17, 2007

(65) Prior Publication Data

US 2008/0086824 A1    Apr. 17, 2008

Related U.S. Application Data

(60) Provisional application No. 60/810,653, filed on Jun. 5, 2006.

(30) Foreign Application Priority Data

May 22, 2006    (FR) .................................. 06 51871

(51) Int. Cl.
*A61Q 5/10* (2006.01)
(52) U.S. Cl. .................. 8/405; 8/406; 8/426; 8/435; 8/547; 8/570; 8/583; 8/606
(58) Field of Classification Search .................. 8/405, 8/406, 426, 435, 547, 570, 583, 606
See application file for complete search history.

(56) References Cited

U.S. PATENT DOCUMENTS

| | | | |
|---|---|---|---|
| 2,848,369 A | 8/1958 | Seemuller | |
| RE30,199 E | 1/1980 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Mockli | |
| 5,733,343 A | 3/1998 | Mockli | |
| 5,766,576 A | 6/1998 | Lowe et al. | |
| 5,792,221 A | 8/1998 | Lagrange et al. | |
| 5,888,252 A | 3/1999 | Mockli | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Blaine | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,060,110 B2 | 6/2006 | Vidal et al. | |
| 7,077,873 B2 | 7/2006 | David et al. | |
| 7,261,743 B2 | 8/2007 | Plos et al. | |
| 7,407,516 B2 | 8/2008 | Vidal | |
| 2002/0095732 A1 | 7/2002 | Kravtchenko et al. | |
| 2003/0084516 A9 | 5/2003 | Kravtchenko et al. | |
| 2005/0074419 A1* | 4/2005 | Guerin ....................... 424/70.6 |
| 2006/0034792 A1 | 2/2006 | Lazzeri et al. | |

FOREIGN PATENT DOCUMENTS

| | | |
|---|---|---|
| DE | 2 359 399 | 6/1975 |
| DE | 3 843 892 | 6/1990 |
| DE | 41 33 957 | 4/1993 |
| DE | 195 43 988 | 5/1997 |
| EP | 0 770 375 | 5/1997 |
| EP | 0 714 954 | 9/2002 |
| EP | 1 627 625 | 2/2006 |
| FR | 2 692 572 | 12/1993 |
| FR | 2 733 749 | 11/1996 |
| FR | 2 750 048 | 12/1997 |

(Continued)

OTHER PUBLICATIONS

STIC Search Report dated Jul. 31, 2008.*

(Continued)

*Primary Examiner*—Eisa B Elhilo
(74) *Attorney, Agent, or Firm*—Finnegan, Henderson, Farabow, Garrett & Dunner, LLP

(57) ABSTRACT

A subject-matter of the present invention is the use, in the direct dyeing of keratinous fibers, of at least one direct dye and of a specific cationic hydrotropic agent of formula:

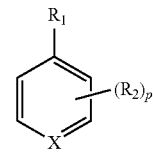

in which X represents CH or $N^+R_6$ with $R_6$ representing a $C_1$-$C_{10}$ alkyl, $R_1$ represents either a hydrogen or a $C_1$-$C_{10}$ alkyl, if X represents $N^+R_6$, or $(CH_2)_n N^+R_3R_4R_5$ with $R_3$, $R_4$ and $R_5$, which are identical or different, representing a $C_1$-$C_{10}$ alkyl and n representing an integer between 0 and 12, if X represents CH; $R_2$ represents a $C_1$-$C_4$ alkyl; p has a value 0 or 1; the electrical neutrality of the compound being provided by a cosmetically acceptable anion or a mixture of cosmetically acceptable anions. The invention likewise relates to a dyeing composition comprising at least one dye and such a cationic hydrotrope and to colouring processes employing this dyeing composition.

17 Claims, No Drawings

FOREIGN PATENT DOCUMENTS

| | | |
|---|---|---|
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 1 026 978 | 4/1966 |
| GB | 1 153 196 | 5/1969 |
| JP | 02 019 576 | 1/1990 |
| JP | 05 163 124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/078660 | 10/2002 |
| WO | WO 02/100369 | 12/2002 |
| WO | WO 02/100834 | 12/2002 |
| WO | WO 03/030842 | 4/2003 |
| WO | WO 2006/131234 | 12/2006 |

OTHER PUBLICATIONS

French Search Report issued in FR 0 651 871 dated Jan. 23, 2007.

* cited by examiner

USE OF A CATIONIC HYDROTROPE FOR THE DIRECT DYEING OF KERATINOUS FIBRES, COMPOSITION COMPRISING IT AND COLOURING PROCESSES EMPLOYING IT

A subject-matter of the present invention is the use of a cationic hydrotropic agent for the direct dyeing of keratinous fibres. It likewise relates to a dyeing composition comprising at least one dye and such a cationic hydrotrope and to colouring processes employing this dyeing composition.

Two colouring methods have been developed in the field of the colouring of keratinous fibres, in particular human keratinous fibres, such as the hair.

The first method, also known as permanent colouring, consists in applying, to the keratinous fibres, compositions comprising oxidation dye precursors, generally known as oxidation bases, such as, for example, ortho- or para-phenylenediamines, ortho- or para-aminophenols, or heterocyclic compounds. These oxidation dye precursors are colourless or weakly coloured compounds which, in combination with oxidizing substances, make possible access, by an oxidative coupling process, to coloured compounds. These coloured compounds, which are insoluble in the dyeing medium, are trapped inside the individual hair.

It is also known that it is possible to vary the shades obtained with these oxidation bases by combining them with couplers or colouring modifiers, the latter being chosen in particular from aromatic meta-diamines, meta-aminophenols, meta-diphenols and certain heterocyclic compounds, such as indole compounds.

The second colouring method, also known as direct or semi-permanent dyeing, consists in applying compositions comprising direct dyes, which are coloured and colouring molecules having an affinity for the fibres and which penetrate by diffusion inside the latter. It is known, for example, to use nitrobenzene, anthraquinone, nitropyridine, azo, xanthene, acridine, azine or triarylmethane direct dyes.

Contrary to the compositions for dyeing by oxidation, the direct dyeing compositions can advantageously be employed without the necessary presence of an oxidizing agent, unless it is desired to have, after the colouring of fibres, a lightening effect on the latter.

With direct colouring, colourings are obtained which are often more chromatic than with oxidation colouring but which are, however, temporary or semipermanent. This is because, due to the nature of the bonds existing between the direct dyes and the keratinous fibre, their desorption from the surface and/or from the core of the fibre takes place relatively easily.

It is obviously possible to employ colourings comprising both oxidation dye precursors and direct dyes.

A great many colouring compositions have been provided to date which are satisfactory in particular in terms of variety of colours and of highlights. However, first, the colourings obtained sometimes lack power and/or homogeneity. Secondly, problems in employing the dyes still continue to be encountered. This is because some dyes or dye precursors may have a solubility limit in conventional dyeing compositions which is not very high, with the consequence, inter alia, of seeing a reduction in the desired colouring effect. In addition, this criterion of solubility reduces the number of dyes which can be used.

One solution in overcoming this disadvantage would be to limit the amount of this or these dyes in the composition. However, in this case, the problems of fall in effectiveness of the colouring, such as, for example, insufficient power of the colour or insufficient covering of white hairs, or excessively high selectivity (difference in colour between the parts of the same fibre and/or between several fibres), would not always be satisfactorily solved.

It is therefore an object of the present invention to solve the abovementioned problems.

These aims and others are achieved by the present invention, a subject-matter of which is thus the use of at least one direct dye and of at least one cationic hydrotrope of following formula (I):

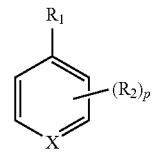

in which:
X represents the CH or $N^+R_6$ group with $R_6$ representing a linear or branched $C_1$-$C_{10}$ alkyl radical;
$R_1$ represents:
a hydrogen atom or a linear or branched $C_1$-$C_{10}$ alkyl radical, if X represents $N^+R_6$, or
a $(CH_2)nN+R3R4R5$ radical with R3, R4 and R5, which are identical or different, representing a linear or branched C1-C10 alkyl radical and n representing an integer between 0 and 12, if X represents CH;
$R_2$ represents a linear or branched C1-C4 alkyl radical;
p has the value 0 or 1;
the electrical neutrality of the compound being provided by a cosmetically acceptable anion or a mixture of cosmetically acceptable anions, for the colouring of keratinous fibres.

A subject-matter of the invention is likewise a dyeing composition comprising, in a medium appropriate for colouring, at least one cationic hydrotrope as defined above and at least one direct dye.

Another subject-matter of the invention is a process for colouring keratinous fibres, in which the following stages are carried out:
a) the abovementioned dyeing composition is applied to the keratinous fibres;
b) the composition is left to stand for a period of time sufficient to obtain the desired effect;
c) the keratinous fibres are optionally rinsed;
d) the fibres are washed with a shampoo and rinsed and then they are dried or left to dry.

The invention also relates to a colouring process in which the stages described above are carried out, with the exception of the fact that stage a) consists in simultaneously or successively applying, to the keratinous fibres, on the one hand the said dyeing composition and on the other hand an oxidizing composition comprising at least one oxidizing agent.

Finally, the invention relates to a process for colouring keratinous fibres in which the stages described above are carried out, with the exception of the fact that the composition applied to the fibres is a ready-for-use composition obtained by mixing a dye composition with a composition comprising at least one oxidizing agent; the cationic hydrotropic agent occurring in the dye composition, in the composition comprising the oxidizing agent or in both these compositions simultaneously.

However, other characteristics and advantages of the present invention will become more clearly apparent on reading the description and examples which will be presented.

In that which follows and unless otherwise indicated, the limits delimiting a range of values are included in this range.

The term "keratinous fibres" is understood to mean more particularly human keratinous fibres, such as the eyelashes, eyebrows and hair. Preferably, the human keratinous fibres are hair.

As was indicated above, the anionic hydrotropic agent employed in the context of the present invention corresponds to the formula (I) below:

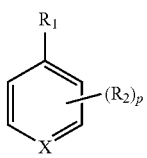

in which:

X represents the CH or $N^+R_6$ group with $R_6$ representing a linear or branched $C_1$-$C_{10}$ alkyl radical, preferably a $C_1$-$C_6$ alkyl radical;

$R_1$ represents:
- a hydrogen atom or a linear or branched $C_1$-$C_{10}$ alkyl radical, preferably a $C_1$-$C_6$ alkyl radical, if X represents $N^+R_6$, or
- a $(CH_2)_nN^+R_3R_4R_5$ radical with $R_3$, $R_4$ and $R_5$, which are identical or different, representing a linear or branched $C_1$-$C_{10}$ alkyl radical and n representing an integer between 0 and 12, if X represents CH;

$R_2$ represents a linear or branched C1-C4 alkyl radical;

p has the value 0 or 1;

the electrical neutrality of the compound being provided by a cosmetically acceptable anion or a mixture of cosmetically acceptable anions.

More particularly, the cosmetically acceptable anion or the mixture of cosmetically acceptable anions is chosen from halides, such as chlorides or bromides; sulphates; alkyl sulphates for which the linear or branched alkyl part is a $C_1$-$C_6$ alkyl part, such as the methosulphate or ethosulphate ions; hydrogencarbonates; perchlorates; salts of carboxylic acids, such as acetates, citrates or tartrates, alone or combined.

Mention may be made, as examples of preferred cationic hydrotropes, without intending to be limited thereto, of:

| | |
|---|---|
| N-Butyl-3,4-dimethyl-pyridinium salt | 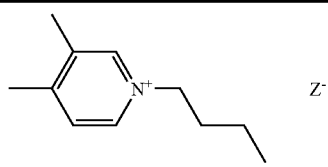 |
| N-Butyl-4-methylpyridinium salt | 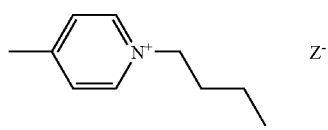 |
| Benzyltriethylammonium salt | 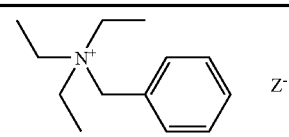 |
| Benzyltrimethylammonium salt | 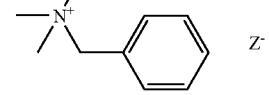 |

In the above formulae, $Z^-$ represents an anion chosen from those mentioned above. Preferably, $Z^-$ represents a chloride ion.

Another subject-matter of the present invention is composed of a dyeing composition comprising, in a medium appropriate for colouring, at least one cationic hydrotrope as just defined and at least one direct dye.

More particularly, the dyeing composition comprises from 0.1 to 50% by weight of cationic hydrotropic agent, with respect to the weight of the dyeing composition, more particularly from 0.1 to 20% by weight and preferably from 1 to 15% by weight, with respect to the weight of the dyeing composition.

The direct dyes which can be used are chosen from ionic or nonionic entities.

Mention may be made, as nonlimiting examples, of nitrobenzene dyes, azo, azomethine, methine, tetraazapentamethine, anthraquinone, naphthoquinone, benzoquinone, phenothiazine, indigoid, xanthene, phenanthridine or phthalocyanine dyes, those derived from triarylmethane and natural dyes, alone or as mixtures.

It can, for example, be chosen from the following red or orangey nitrobenzene dyes:

1-hydroxy-3-nitro-4-[N-(γ-hydroxypropyl)amino]-benzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-[N-(β-hydroxyethyl)amino]benzene,
1,4-diamino-2-nitrobenzene,
1-amino-2-nitro-4-(methylamino)benzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyl-oxy)benzene,
1-(β,γ-dihydroxypropyl)oxy-3-nitro-4-[(β-hydroxyethyl)amino]benzene,
1-hydroxy-3-nitro-4-aminobenzene,
1-hydroxy-2-amino-4,6-dinitrobenzene,
1-methoxy-3-nitro-4-[(β-hydroxyethyl)amino]benzene,
2-nitro-4'-hydroxydiphenylamine,
1-amino-2-nitro-4-hydroxy-5-methylbenzene,
2-[4-(2-chloro-4-nitrophenylazo)-N-ethylphenylamino]-ethanol (Disperse Red 13).

The direct dye can also be chosen from yellow and green-yellow nitrobenzene direct dyes. Mention may be made, for example, of the compounds chosen from:

1-β-hydroxyethyloxy-3-methylamino-4-nitrobenzene,
1-methylamino-2-nitro-5-[(β,γ-dihydroxypropyl)-oxy]benzene, 1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitro-chlorobenzene,
4-(β-hydroxyethyl)amino-3-nitro-methylbenzene,
4-(β,γ-dihydroxypropyl)amino-3-nitro-trifluoromethyl-benzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitro-benzene,
1-(β-hydroxyethyl)amino-2-nitrobenzene,
4-(β-hydroxyethyl)amino-3-nitrobenzamide.

Mention may also be made of blue or purple nitrobenzene direct dyes, such as, for example:
1-(β-hydroxyethyl)amino-4-[N,N-bis(β-hydroxyethyl)-amino]-2-nitrobenzene,
1-(γ-hydroxypropyl)amino-4-[N,N-bis(β-hydroxyethyl)-amino]-2-nitrobenzene,
1-(β-hydroxyethyl)amino-4-[(N-methyl, N-β-hydroxyethyl)amino]-2-nitrobenzene,
1-(β-hydroxyethyl)amino-4-[(N-ethyl, N-β-hydroxyethyl)amino]-2-nitrobenzene,
1-(β,γ-dihydroxypropyl)amino-4-[(N-ethyl, N-β-hydroxyethyl)amino]-2-nitrobenzene, the 2-nitro-para-phenylenediamines of following formula:

in which:
Rb represents a $C_1$-$C_4$ alkyl radical or a β-hydroxyethyl or β-hydroxypropyl or γ-hydroxypropyl radical;
Ra and Rc, which are identical or different, represent a β-hydroxyethyl, β-hydroxypropyl, γ-hydroxypropyl or β,γ-dihydroxypropyl radical, one at least of the Rb, Rc or Ra radicals representing a γ-hydroxypropyl, radical and Rb and Rc not being able to simultaneously denote a β-hydroxyethyl radical when Rb is a γ-hydroxypropyl radical, such as those described in French Patent FR 2 692 572.

Mention may also be made, among the azo direct dyes which can be used according to the invention, of the cationic azo dyes described in Patent Applications WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078660, WO 02/100834, WO 02/100369 and FR 2 844 269.

Mention may very particularly be made, among these compounds, of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]-pyridinium methyl sulphate.

Mention may also be made, among azo direct dyes, of the following dyes described in the Colour Index International, 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24 and Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Mention may be made, among quinone direct dyes, of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15 and Basic Blue 99, and of the following compounds:
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone,
1,4-bis (β,γ-dihydroxypropylamino)anthraquinone.

Mention may be made, among azine dyes, of the following compounds: Basic Blue 17 and Basic Red 2.

Mention may be made, among the triarylmethane dyes which can be used according to the invention, of the following compounds: Basic Green 1, Acid Blue 9, Basic Violet 3, Basic Violet 14, Basic Blue 7, Acid Violet 49, Basic Blue 26 and Acid Blue 7.

Mention may be made, among the indoamine dyes which can be used according to the invention, of the following compounds:
2-β-hydroxyethylamino-5-[bis(β-4'-hydroxyethyl)amino]anilino-1,4-benzoquinone,
2-β-hydroxyethylamino-5-(2'-methoxy-4'-amino)anilino-1,4-benzoquinone,
3-N-(2'-chloro-4'-hydroxy)phenylacetylamino-6-methoxy-1,4-benzoquinone imine,
3-N-(3'-chloro-4'-methylamino)phenylureido-6-methyl-1,4-benzoquinone imine,
3-[4'-N-(ethyl, carbamylmethyl)amino]phenylureido-6-methyl-1,4-benzoquinone imine.

Mention may in particular be made, among the dyes of tetraazapentamethine type which can be used according to the invention, of 2-((E)-{(E)-[(1,3-dimethyl-1,3-dihydro-2H-imidazol-2-ylidene)hydrazono]methyl}-diazenyl)-1,3-dimethyl-1H-imidazol-3-ium chloride, 2-{(E)-[(1Z)-N-(1,3-dimethyl-1,3-dihydro-2H-imidazol-2-ylidene) ethanehydrazonoyl]diazenyl}-1,3-dimethyl-1H-imidazol-3-ium chloride, 4-methoxy-2-((E)-{(1E)-1-[(2E)-(4-methoxy-1-methylpyridin-2(1H)-ylidene)-hydrazono] ethyl}diazenyl)-1-methylpyridinium chloride, 1-methyl-2-((E)-{(1E)-1-[(2E)-(1-methylpyridin-2(1H)-ylidene) hydrazono]ethyl}diazenyl)pyridinium chloride, 1-(2-hydroxyethyl)-2-[(E)-((1E)-1-{(2E)-[1-(2-hydroxyethyl)pyridin-2(1H)-ylidene]hydrazono}ethyl)-diazenyl] pyridinium chloride, 1-methyl-2-((E)-{(E)-[(2Z)-(1-methylpyridin-2(1H)-ylidene)hydrazono]methyl}-diazenyl) pyridinium chloride or 1-(2-hydroxyethyl)-2-[(E)-((E)-{(2E)-[1-(2-hydroxyethyl)pyridin-2(1H)-ylidene] hydrazono}methyl)diazenyl]pyridinium acetate.

Mention may be made, among the natural direct dyes which can be used according to the invention, of lawsone, juglone, alizarin, purpurin, carminic acid, kermesic acid, purpurogallin, protocatechualdehyde, indigo, isatin, curcumin, spinulosin or apigenidin. Use may also be made of the extracts or decoctions comprising these natural dyes and in particular cataplasms or henna-based extracts.

Azo dyes are of particular use in the present invention.

The content of direct dye(s) in the dyeing composition generally varies from 0.001 to 20% by weight, with respect to the weight of the dyeing composition, and preferably from 0.01 to 10% by weight.

The composition of the invention can also comprise oxidation dyes, it being possible for the latter to be chosen from oxidation bases, couplers or their mixtures.

More particularly, the oxidation bases can be chosen from the oxidation bases conventionally used in oxidation dyeing, for example para-phenylenediamines, bisphenylalkylenediamines, para-aminophenols, ortho-aminophenols and heterocyclic bases.

Mention may more particularly be made, among para-phenylenediamines, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylene-diamine, N,N-(ethyl,β-hydroxyethyl)-para-phenylene-diamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylene-diamine, 4-aminophenylpyrrolidine, 2-thienyl-para-phenylenediamine, 2-(β-hydroxyethylamino)-5-aminotoluene and their addition salts with an acid.

Among the para-phenylenediamines mentioned above, para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their addition salts with an acid are particularly preferred.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-amino-phenyl)tetramethylenediamine, N,N'-bis(4-methylamino-phenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane and their addition salts with an acid.

Mention may be made, among para-aminophenols, by way of example, of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl) phenol, 4-amino-2-(methoxy-methyl)phenol, 4-amino-2-(aminomethyl)phenol, 4-amino-2-((β-hydroxyethyl) aminomethyl)phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts with an acid.

Mention may be made, among heterocyclic bases, by way of example, of pyridine derivatives, pyrimidine derivatives and pyrazole derivatives.

Mention may be made, among pyridine derivatives, of the compounds disclosed, for example, in Patents GB 1 026 978 and GB 1 153 196, such as 2,5-diaminopyridine, 2-[(4-methoxyphenyl)amino]-3-aminopyridine, 2,3-diamino-6-methoxypyridine, 2-[(β-methoxyethyl)amino]-3-amino-6-methoxypyridine, 3,4-diaminopyridine and their addition salts with an acid.

Mention may be made, among pyrimidine derivatives, of the compounds disclosed, for example, in Patents DE 2 359 399; JP 88-169 571; JP 05 163 124; EP 0 770 375 or Patent Application WO 96/15765, such as 2,4,5,6-tetraminopyrimidine, 4-hydroxy-2,5,6-triamino-pyrimidine, 2-hydroxy-4,5,6-triaminopyrimidine, 2,4-dihydroxy-5,6-diaminopyrimidine or 2,5,6-triamino-pyrimidine, and pyrazolopyrimidine derivatives, such as those mentioned in Patent Application FR-A-2 750 048 and among which may be mentioned pyrazolo[1,5-a]-pyrimidine-3,7-diamine; 2,5-dimethylpyrazolo[1,5-a]-pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol, 2-(7-amino-pyrazolo[1,5-a]pyrimidin-3-ylamino)ethanol, 2-[(3-aminopyrazolo[1,5-a]pyrimidin-7-yl)(2-hydroxy-ethyl)amino]ethanol, 2-[(7-aminopyrazolo[1,5-a]-pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropyl-amino)pyrazolo[1,5-a]pyrimidine and their addition salts with an acid and their tautomeric forms, when a tautomeric equilibrium exists.

Mention may be made, among pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxy-ethyl)-3-methylpyrazole, 4,5-diamino-1-ethyl-3-methyl-pyrazole, 4,5-diamino-1-ethyl-3-(4'-methoxyphenyl)-pyrazole, 4,5-diamino-1-ethyl-3-(hydroxymethyl)-pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-tri-aminopyrazole, 1-methyl-3,4,5-triaminopyrazole, 3,5-diamino-1-methyl-4-(methylamino) pyrazole, 3,5-diamino-4-(β-hydroxyethyl)amino-1-methylpyrazole and their addition salts with an acid.

When the dyeing composition comprises one or more oxidation bases, their content is usually between 0.001 and 10% by weight of the weight of the dyeing composition and preferably between 0.005 and 6% by weight.

The composition of the invention can comprise couplers, the latter can be chosen from those conventionally used for the colouring of keratinous fibres.

Mention may in particular be made of meta-phenylenediamines, meta-aminophenols, meta-diphenols, naphthalene couplers and heterocyclic couplers.

Mention may be made, by way of example, of 2-methyl-5-aminophenol, 5-N-(β-hydroxyethyl)amino-2-methyl-phenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl-amino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxy-ethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxy-pyr-idine, 1-N-(β-hydroxyethyl)amino-3,4-methylenedioxybenzene, 2,6-bis(β-hydroxyethylamino)toluene and their addition salts with an acid.

If the composition comprises one or more couplers, their content conventionally represents from 0.001 to 10% by weight of the weight of the dyeing composition and preferably from 0.005 to 6% by weight.

Generally, the addition salts with an acid are chosen, for example, from hydrochlorides, hydrobromides, sulphates, citrates, succinates, tartrates, lactates, tosylates, benzenesulphonates, phosphates and acetates.

Furthermore, it is specified that the dyeing composition does not comprise an oxidizing agent.

The medium appropriate for dyeing generally comprises water or a mixture of water and of at least one organic solvent in order to dissolve the compounds which would not be sufficiently soluble in the water.

More particularly, the organic solvents are chosen from linear or branched, preferably saturated, monoalcohols or diols comprising 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols, such as benzyl alcohol or phenylethyl alcohol; glycols or glycol ethers, such as, for example, ethylene glycol monomethyl, monoethyl and monobutyl ethers, propylene glycol or its ethers, such as, for example, propylene glycol monomethyl ether, butylene glycol or dipropylene glycol; and diethylene glycol alkyl ethers, in particular $C_1$-$C_4$ alkyl ethers, such as, for example, diethylene glycol monoethyl ether or monobutyl ether, alone or as a mixture.

The usual solvents described above, if they are present, generally represent from 1 to 40% by weight, preferably from 5 to 30% by weight, with respect to the weight of the dyeing composition.

According to an advantageous alternative form of the invention, the dyeing composition comprises at least 40% by weight of water, with respect to the weight of the dyeing composition, preferably at least 70% by weight of water.

The dyeing composition employed in the context of the invention can also include various adjuvants conventionally used in compositions for dyeing keratinous fibres, such as anionic, cationic, nonionic, amphoteric or zwitterionic surface-active agents or their mixtures, anionic, cationic, nonionic, amphoteric or zwitterionic polymers or their mixtures, inorganic or organic thickening agents and in particular anionic, cationic, nonionic and amphoteric polymeric associative thickeners, antioxidants, penetration agents, sequestering agents, fragrances, buffers, dispersing agents, conditioning agents, such as, for example, volatile or nonvolatile and modified or unmodified silicones, film-forming agents, ceramides, preservatives or opacifying agents.

Preferably, the dyeing composition comprises at least one surface-active agent, one polymer or their mixtures.

The above adjuvants are generally present in amounts, for each of them, of between 0.01 and 20% by weight, with respect to the weight of the dyeing composition.

Of course, a person skilled in the art will take care to choose this or these possible adjuvants in such a way that the advantageous properties intrinsically attached to the dyeing composition employed in the context of the invention are not, or not substantially, detrimentally affected by the envisaged addition or additions.

The pH of the dyeing composition is generally between 2 and 12 approximately and preferably between 5 and 11 approximately. It can be adjusted to the desired value using acidifying or basifying agents commonly used in the dyeing of keratinous fibres or alternatively using conventional buffering systems.

Mention may be made, among acidifying agents, by way of example, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among basifying agents, by way of example, of aqueous ammonia, alkaline carbonates, alkanolamines, such as mono-, di- and triethanolamine and their derivatives, sodium hydroxide, potassium hydroxide and the compounds of the following formula:

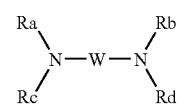

in which W is a propylene residue optionally substituted by a hydroxyl group or a $C_1$-$C_4$ alkyl radical and $R_a$, $R_b$, $R_c$ and $R_d$, which are identical or different, represent a hydrogen atom or a $C_1$-$C_4$ alkyl or $C_1$-$C_4$ hydroxyalkyl radical.

It should be noted that the dyeing composition can be provided in various forms, such as in the form of liquids, creams, gels or pastes or in any other form appropriate for carrying out dyeing of keratinous fibres and in particular of human hair.

Another subject-matter according to the invention is a process for colouring keratinous fibres in which the following stages are carried out:
  a) a dyeing composition as has just been described in detail is applied to the said fibres;
  b) the said composition is left to stand for a period of time sufficient to obtain the desired effect,
  c) the keratinous fibres are optionally rinsed;
  d) the fibres are washed with a shampoo and rinsed and then they are dried or left to dry.

This alternative form is particularly appropriate in the case where the dyeing composition does not comprise an oxidation dye.

Another subject-matter of the invention is composed of a process consisting in carrying out the following stages:

a) on the one hand, a dyeing composition as defined above and, on the other hand, an oxidizing composition comprising at least one oxidizing agent are applied to the keratinous fibres, simultaneously or successively;
b) the mixture is left to stand for a period of time sufficient to obtain the desired effect;
c) the keratinous fibres are optionally rinsed;
d) the fibres are washed with a shampoo and rinsed and then they are dried or left to dry.

It should be noted that this process alternative form is appropriate if the dyeing composition comprises at least one dye precursor, such as oxidation bases and couplers, or also if the composition comprises one or more direct dyes and if it is desired to obtain a lightening effect on the keratinous fibres to be treated.

The oxidizing composition mixed with the dyeing composition comprises at least one oxidizing agent chosen from those conventionally employed in this field.

The latter are, for example, hydrogen peroxide, urea hydrogen peroxide, alkali metal bromates, persalts, such as perborates and persulphates, peracids and oxidase enzymes, among which may be mentioned peroxidases, 2-electron oxidoreductases, such as uricases, and 4-electron oxygenases, such as laccases.

According to a specific embodiment, the composition comprises an oxidizing agent of peroxide type and/or an oxidizing agent of persalts type, for example a hydrogen peroxide and persulphates mixture or hydrogen peroxide alone.

The content of oxidizing agent is generally between 1 and 60% by weight, with respect to the weight of ready-for-use composition, preferably between 1 and 40% by weight, with respect to the weight of the ready-for-use composition.

The oxidizing composition can also include various adjuvants conventionally used in compositions for dyeing keratinous fibres and as defined above in the context of the description of the dyeing composition.

The pH of the oxidizing composition is such that, after mixing with the dyeing composition, the pH of the ready-for-use composition applied to the keratinous fibres advantageously varies between 4 and 12 approximately and preferably between 7 and 11.5. It can be adjusted to the desired value using acidifying or basifying agents commonly used in dyeing keratinous fibres and as defined above.

Generally, the oxidizing composition used is an aqueous composition and can occur in the form of a solution or also of an emulsion.

Generally, the dyeing composition is mixed with approximately 0.5 to 10 equivalents by weight of the oxidizing composition.

A final subject-matter of the invention is composed of a process for colouring keratinous fibres in which the following stages are carried out:
a) a ready-for-use composition is prepared by mixing a dye composition comprising, in a medium appropriate for colouring, at least one dye or one dye precursor with an oxidizing composition comprising at least one oxidizing agent; the anionic hydrotropic agent occurring in the dye composition, in the composition comprising the oxidizing agent or in both these compositions simultaneously,
b) the ready-for-use composition thus obtained is applied to the keratinous fibres and is left to stand for a period of time sufficient to obtain the desired effect,
c) the keratinous fibres are optionally rinsed,
d) the fibres are washed with a shampoo and rinsed and then they are dried or left to dry.

This process is particularly appropriate if the composition applied to the fibres comprises at least one dye precursor, such as oxidation bases and couplers, or also if the composition comprises one or more direct dyes and if it is desired to obtain a lightening effect on the keratinous fibres to be treated.

Preferably, the composition comprises at least one direct dye.

The dye composition employed in this process corresponds to the dyeing composition which was described above, except for the fact that it does not comprise the cationic hydrotrope.

According to a first alternative form, the cationic hydrotrope is present in the dye composition. In this case, the dye composition exhibits the characteristics of the dyeing composition described above.

According to a second alternative form, the hydrotrope is present in the oxidizing composition. In this case, its content is such that it comes within the ranges of concentrations given above, expressed with respect to the weight of the dyeing composition, that is to say with respect to the weight of the dye composition and of the cationic hydrotrope.

The third alternative form represents a combination of the two preceding alternative forms.

That which was indicated above relating to the dyeing composition and the oxidizing composition remains valid and reference may be made thereto for further details.

According to this process, the dye (or dyeing) and oxidizing compositions are applied simultaneously or successively, with or without intermediate rinsing.

According to the process employed, the dyeing composition, the ready-for-use composition and optionally the oxidizing composition are applied to the dry or wet keratinous fibres and are then left for a leave-in time sufficient to obtain the desired colouring.

Whatever the alternative form selected (with or without oxidizing agent), the leave-in time is generally between a few seconds and one hour, preferably between 3 and 30 minutes.

In the case where the dyeing and oxidizing compositions are applied successively, the leave-in time of each of them varies within the same ranges as those indicated above.

The temperature at which the composition is left to act is generally between 15 and 220° C., more particularly between 15 and 80° C. and preferably between 15 and 40° C.

At the end of the leave-in time, the composition applied is removed by rinsing with water, optionally followed by washing with a shampoo and then optionally by drying.

The following examples illustrate the invention without, however, limiting the scope thereof.

EXAMPLE 1

A dyeing composition is prepared comprising the dye Disperse Red 13 at 0.5% in a mixture composed of 15% of ethanol, of 5% of benzyl alcohol, of 2% of N-butyl-3,4-dimethylpyridinium chloride and of 78% of water (percentages expressed by weight).

The composition is applied to a lock of hair comprising 90% of natural hairs and to a lock of hair comprising 90% of permed hairs, and is left to stand for 20 minutes.

After rinsing and drying, the locks are coloured red in a powerful homogeneous way.

EXAMPLE 2

A dyeing composition is prepared comprising the dye Disperse Red 13 at 0.25% in a mixture composed of 15% of ethanol, of 5% of benzyl alcohol, of 2% of benzenetriethylammonium chloride and of 75% of water (percentages expressed by weight).

The composition is subsequently applied to a lock of hair comprising 90% of natural hairs and to a lock of hair comprising 90% of permed hairs, and is left to stand for 20 minutes.

After rinsing and drying, the locks are coloured red in a powerful homogeneous way.

What is claimed is:

1. A method for dyeing keratinous fibers comprising applying to the keratinous fibers a dyeing composition comprising at least one direct dye and at least one cationic hydrotrope of following formula (I):

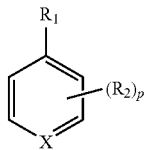

in which:
  X represents the CH or $N^+R_6$ group with $R_6$ representing a linear or branched $C_1$-$C_{10}$ alkyl radical;
  $R_1$ represents:
    a hydrogen atom or a linear or branched $C_1$-$C_{10}$ alkyl radical, if X represents $N^+R_6$, or
    a $(CH_2)_nN^+R_3R_4R_5$ radical with $R_3$, $R_4$ and $R_5$, which are identical or different, representing a linear or branched $C_1$-$C_{10}$ alkyl radical and n representing an integer between 0 and 12, if X represents CH;
  $R_2$ represents a linear or branched C1-C4 alkyl radical; and
  p has the value 0 or 1;
    wherein the electrical neutrality of the compound is provided by a cosmetically acceptable anion or a mixture of cosmetically acceptable anions, and
    wherein the dyeing composition does not comprise benzyltrimethyammonium salt or benzyltriethylammonium salt.

2. The method according to claim 1, wherein the cosmetically acceptable anion or the mixture of cosmetically acceptable anions is chosen from halides; sulphates; alkyl sulphates for which the linear or branched alkyl part is a $C_1$-$C_6$ alkyl part, including the methosulphate or ethosulphate ions; hydrogencarbonates; perchlorates; and salts of carboxylic acids, including acetates, citrates, or tartrates, alone or combined.

3. The method according to claim 1, wherein the at least one cationic hydrotrope of formula (I) is chosen from N-butyl-3,4-dimethylpyridinium or N-butyl-4-methylpyridinium alone or as mixtures.

4. A dyeing composition for coloring human keratinous fibers, comprising, in a medium appropriate for colouring, at least one cationic hydrotrope and at least one direct dye, wherein the at least one cationic hydrotrope has the following formula (II):

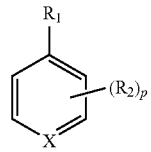

in which:
  X represents the CH or $N^+R_6$ group with $R_6$ representing a linear or branched $C_1$-$C_{10}$ alkyl radical;
  $R_1$ represents:
    a hydrogen atom or a linear or branched $C_1$-$C_{10}$ alkyl radical, if X represents $N^+R_6$, or
    a $(CH_2)_nN^+R_3R_4R_5$ radical with $R_3$, $R_4$ and $R_5$, which are identical or different, representing a linear or branched $C_1$-$C_{10}$ alkyl radical and n representing an integer between 0 and 12, if X represents CH;
  $R_2$ represents a linear or branched C1-C4 alkyl radical; and
  p has the value 0 or 1;
    wherein the electrical neutrality of the compound is provided by a cosmetically acceptable anion or a mixture of cosmetically acceptable anions, and
    wherein the dyeing composition does not comprise benzyltrimethyammonium salt or benzyltriethylammonium salt.

5. The dyeing composition according to claim 4, wherein the concentration of the at least one cationic hydrotrope ranges from 0.5% to 50% by weight, with respect to the weight of the dyeing composition.

6. The dyeing composition according to claim 4, wherein the at least one direct dye is chosen from ionic or nonionic direct dyes.

7. The dyeing composition according to claim 4, wherein the concentration of the at least one direct dye ranges from 0.001% to 20% by weight, with respect to the weight of the dyeing composition.

8. The dyeing composition according to claim 4, wherein the dyeing composition further comprises at least one oxidation base and/or at least one coupler.

9. The dyeing composition according to claim 8, wherein the at least one oxidation base is chosen from o-phenylenediamines, p-phenylenediamines, double bases, o-aminophenols, p-aminophenols, heterocyclic bases, their acid addition salts and mixtures thereof.

10. The dyeing composition according to claim 4, wherein the concentration of the at least one oxidation base ranges from 0.001% to 10% by weight, with respect to the weight of the dyeing composition.

11. The dyeing composition according to claim 4, wherein the coupler is chosen from m-aminophenols, m-phenylenediamines, m-diphenols, naphthols, heterocyclic couplers, their acid addition salts, and mixtures thereof.

12. The dyeing composition according to claim 4, wherein the concentration of the coupler ranges from 0.001% to 10% by weight, with respect to the weight of the dyeing composition.

13. The dyeing composition according to claim 4, wherein the dyeing composition comprises at least 40% by weight of water, with respect to the weight of the dyeing composition.

14. The dyeing composition according to claim 4, wherein the dyeing composition comprises at least one surfactant and/or at least one polymer.

15. A process for coloring keratinous fibers, comprising:
  a) applying the dyeing composition according to claim 4 to the keratinous fibers;

b) leaving the composition to stand for a period of time sufficient to obtain a desired effect;
c) optionally rinsing the keratinous fibers; and
d) washing the fibers with a shampoo, rinsing the fibers, and drying or leaving to dry the fibers.

16. A process for coloring keratinous fibers, comprising:
a) applying a mixture comprising the dyeing composition according to claim 4 and an oxidizing composition comprising at least one oxidizing agent to the keratinous fibers, simultaneously or successively;
b) leaving the mixture to stand for a period of time sufficient to obtain a desired effect;
c) optionally rinsing the keratinous fibers; and
d) washing the fibers with a shampoo, rinsing the fibers, and drying or leaving to dry the fibers.

17. A process for coloring keratinous fibers, comprising:
a) preparing a ready-for-use composition by mixing a dye composition comprising, in a medium appropriate for coloring, at least one direct dye and/or at least one oxidation dye with a composition comprising at least one oxidizing agent; wherein at least one cationic hydrotropic agent is present in the dye composition, in the composition comprising the oxidizing agent, or in both these compositions simultaneously,
b) applying the ready-for-use composition to the keratinous fibers and leaving the ready-for-use composition to stand for a period of time sufficient to obtain a desired effect;
c) optionally rinsing the keratinous fibers;
d) washing the fibers with a shampoo, rinsing the fibers, and drying or leaving to dry the fibers;

wherein the cationic hydrotrope has the following formula (III):

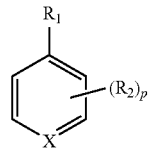

in which:
X represents the CH or $N^+R_6$ group with $R_6$ representing a linear or branched $C_1$-$C_{10}$ alkyl radical;
$R_1$ represents:
a hydrogen atom or a linear or branched $C_1$-$C_{10}$ alkyl radical, if X represents $N^+R_6$, or
a $(CH_2)_n N^+R_3R_4R_5$ radical with $R_3$, $R_4$ and $R_5$, which are identical or different, representing a linear or branched $C_1$-$C_{10}$ alkyl radical and n representing an integer between 0 and 12, if X represents CH;
$R_2$ represents a linear or branched C1-C4 alkyl radical; and
p has the value 0 or 1;
wherein the electrical neutrality of the compound is provided by a cosmetically acceptable anion or a mixture of cosmetically acceptable anions, and
wherein the dyeing composition does not comprise benzyltrimethyammonium salt or benzyltriethylammonium salt.

* * * * *